United States Patent [19]

Giddings

[11] Patent Number: 4,830,756

[45] Date of Patent: May 16, 1989

[54] HIGH SPEED SEPARATION OF ULTRA-HIGH MOLECULAR WEIGHT POLYMERS BY HYPERLAYER FIELD-FLOW FRACTIONATION

[75] Inventor: John C. Giddings, Salt Lake City, Utah

[73] Assignee: University of Utah, Salt Lake City, Utah

[21] Appl. No.: 217,707

[22] Filed: Jul. 11, 1988

[51] Int. Cl.[4] ............................................. B03B 5/00
[52] U.S. Cl. .................................. 210/739; 210/748; 210/775; 210/789
[58] Field of Search .................. 209/155, 1, 208, 209, 209/11, 444, 453; 210/775, 646, 748, 695, 739, 774, 789, 801–804

[56] References Cited

U.S. PATENT DOCUMENTS

3,449,938  6/1969  Giddings .......................... 210/775
4,147,621  4/1979  Giddings .......................... 210/646
4,214,981  6/1980  Giddings .......................... 210/748
4,440,638  4/1984  Judy et al. ....................... 210/748

Primary Examiner—Frank Sever

[57] ABSTRACT

A process for high speed separation of ultra-high molecular weight polymers using a hyperlayer field-flow fractionation technique comprising forcing a carrier fluid containing a small sample of the high molecular weight polymer through a thin flow channel possessing an accumulation wall, applying a primary externally controlled driving force transversely across the thin dimension of the channel, adjusting the flowrate of the fluid and the field strength of the primary externally controlled force in relationship to the channel thickness such that at least over part of the molecular weight range the entropic force $F_e$ and the primary driving force $F_1$ are related by the inequality $|F_e| > |F_1|$ at the accumulation wall of the channel.

19 Claims, 4 Drawing Sheets

HIGH SPEED SEPARATION OF ULTRA-HIGH MOLECULAR WEIGHT POLYMERS BY HYPERLAYER FIELD-FLOW FRACTIONATION

BACKGROUND OF THE INVENTION

1. Field of the Invention

This invention relates to a new process for polymer fractionation. More particularly, the invention relates to a modified FFF process for the separation of polymers having ultra-high molecular weight which gives faster and higher resolution than possible heretofore for such polymers.

Specifically, the invention provides a new process for high speed separation of ultra-high molecular weight polymers, e.g. polymers having a molecular weight higher than $1 \times 10^6$, by a hyperlayer field-flow fractionation technique. The new process broadly comprises forcing a carrier fluid containing a small sample of the said ultra-high molecular weight polymer through a thin flow channel, applying a primary externally controlled driving force transversely across the thin dimension of the channel, adjusting the flowrate of the fluid and the field strength governing the primary externally controlled force in relationship to the channel thickness such that at least over part of the molecular weight range the entropic force $F_e$ and the primary driving force $F_1$ are related by the inequality $$|F_e| > |F_1|$$

at the accumulation wall of the channel.

2. Prior Art

There is a growing need in industry and health sciences for the separation of polymeric and macromolecular material whose components include various kinds of high molecular weight species including polysaccharides, DNA, synthetic polymers and the like.

Various methods have been proposed but in general, they have been too slow, too low in throughput, too labor intensive, too expensive or have failed to effect the separation with the desired degree of resolution.

Some of the highest resolution techniques disclosed have been those based on field-flow fractionation as disclosed in U.S. Pat. No. 3,449,938 and U.S. Pat. No. 4,147,621, but their operation is relatively slow and difficult for ultra-high molecular weight polymers. Various form of electrophoresis have been used for charged biopolymers, but the separation is slow and the operation inconvenient and labor intensive because electrophoresis is a nonelution technique for which sample collection is difficult. Chromotography has been used widely for low and medium sized molecules but is not particularly suited for the fractionation of ultra-high molecular weight polymers because of adsorption, degradation and sample loss problems.

The prior known methods thus present serious defects in meeting the needs of industry particularly in biotechnology and polymer processing. The increasing competitiveness of industry and the rapid evolution of new technologies is now putting extraordinary demands on analytical separation processes for use in process control and product analysis.

There is thus a rapidly growing need for new separation technology applicable to polymers for which the resolution is high and the separation is fast. In addition, because of the enormous variety of separation needs, the separation process should be preferably based on as large a variety of molecule properties as possible.

It is an object of the invention, therefore, to provide a new and efficient process for the fractionation of high molecular weight polymers. It is a further object to provide a new process for the separation of high molecular weight polymers from fluid media which can be accomplished in a very rapid and efficient manner. It is a further object to provide a new process for high molecular weight polymer fractionation which permits a very high resolution of separation. It is a further object of the invention to provide a fractionation operating as an elution technique in which fractions can be conveniently collected from the eluting stream. It is a further object to provide a new process for fractionation of polymers which is particularly effective with ultra-high molecular weight polymers which can be rigid or flexible. It is a further object to provide a fractionation process which is economical to operate and uses inexpensive equipment. These and other objects will be apparent from the following detailed description thereof.

SUMMARY OF THE INVENTION

It has now been discovered that these and other objects can be accomplished by the new process of the present invention which comprises a very rapid and efficient process for the separation of very high molecular weight polymers.

The new process of the invention comprises an improvement in the field-flow fractionation process wherein a carrier fluid containing a small sample of the high molecular weight polymer is forced through a thin flow channel in which one of the walls becomes an accumulation wall, a primary externally controlled driving force is applied transversely across the thin dimension of the channel, the flowrate of the fluid and the field strength of the primary externally controlled driving force are adjusted in relationship to the channel thickness such that at least over part of the molecular weight range the entropic force $F_e$ and the primary driving force $F_1$ are related by the inequality $$|F_e > |F_1|$$

at the accumulation wall of the channel.

It has been surprisingly found that this process solves many of the defects of the prior known techniques and presents for the first time a highly efficient process for the fractionation of very high molecular weight polymers. The new process is very rapid and effects the desired separation of such high molecular weight polymers in a matter of minutes. In addition, the resolution into the various polymer fractions is surprisingly high and far superior to any known techniques that could be used for the separation of high molecular weight polymers.

DESCRIPTION OF THE DRAWINGS

The various objects and features of the present invention will be more fully understood by reference to the accompanying drawings.

DETAILED DESCRIPTION OF THE DRAWINGS

Figure 1:
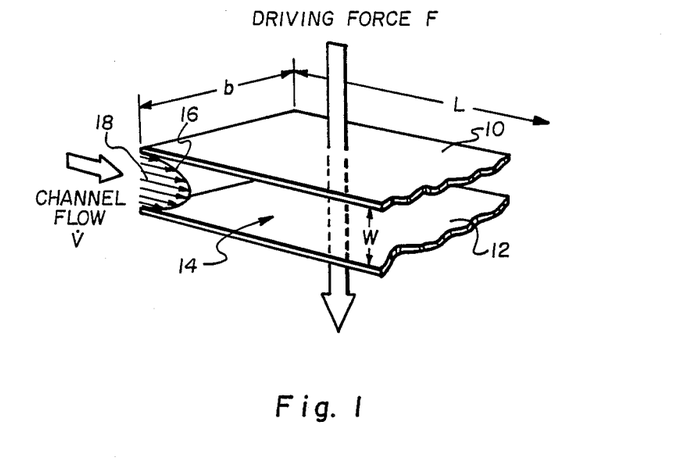
FIG. 1 is a partial cutaway showing the prospective use of a flow channel.

Referring now to the drawings:

Referring to FIG. 1, the basic concept of FFF is represented by the flow vectors $\dot{V}$ and the driving force vector F. These vectors are drawn in relation to two closely spaced, parallel plate means, 10 and 12. The region between these plates is identified as a flow channel 14, through which the fluid is conducted. This fluid flow is represented by a channel profile 16 which shows relative fluid movement by means of channel flow vector 18, with the average channel flow represented by single flow vectors $\dot{V}$. B is the breadth, L the length and w the tickness of the channel.

A primary driving force is imposed normal to channel flow for the purpose of controlling the transverse positions of polymers. This driving force is illustrated as F oriented perpendicular to the channel flow V and the respective plate means. The plate means 12 is the channel wall toward which polymer is driven by the primary driving force and is termed the "accumulation wall."

Figure 2:
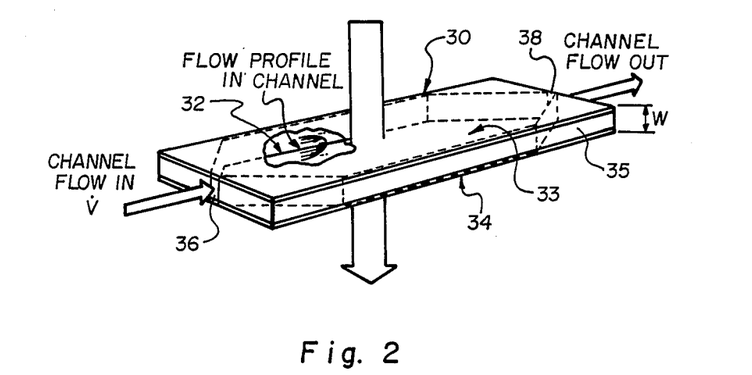
FIG. 2 depicts an FFF flow channel with enclosed structure around the channel.

The structure can be implemented by many variations of basic elements as shown in FIG. 2. The flow channel 32 is substantially defined by a first and second plate means 33 and 34. Side wall structures 30 and 35 provide the respective plate means to fully enclose the chamber region 32. Since no flow should occur through the side walls, they must be of non-porous material. A general configuration might comprise a spacer plate 35 (also referred to as the side wall) having the desired thickness w interposed between respective nonpermeable or semi-permeable plates, the combination being tightly clamped together.

Inlet means 36 and outlet means 38 are provided at opposite ends of the chamber to enable channel flow there between. Control means associated therewith are desirable to facilitate adjustment of $\dot{V}$. Typically, the outlet end will feed effluent to detection means for obtaining separation results.

Figure 3A:
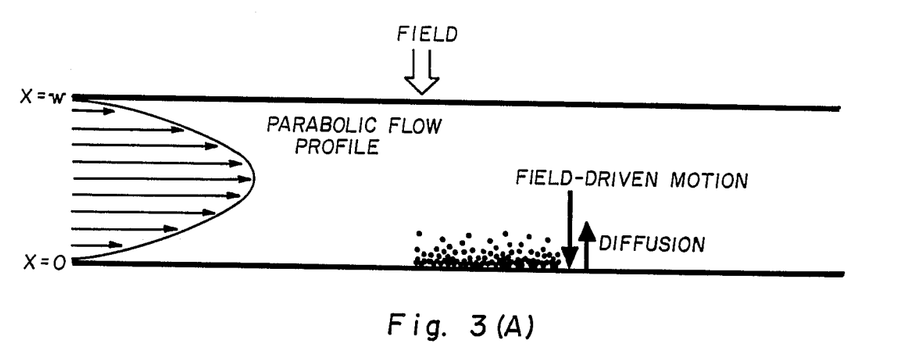
FIG. 3 is a sketch illustrating the distribution of a polymer sample in both normal FFF (A) and entropy-driven hyperlayer FFF (B).

FIG. 3 is a sketch illustrating the distribution of a polymer sample in the normal FFF as in sketch (a) and the distribution with entropy-driven hyperlayer FFF as in sketch (B).

Figure 4:
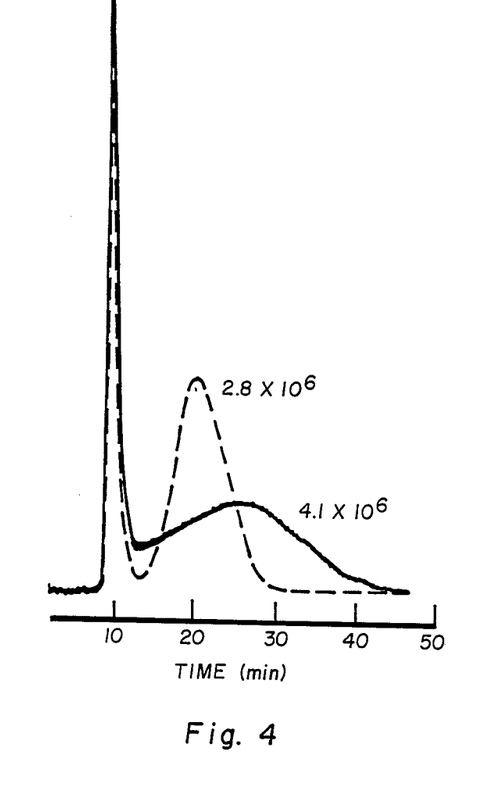
FIG. 4 is a reproduction of fractograms obtained for two polystyrene polymer standards with weight average molecular weights of $2.8 \times 10^6$ and $4.1 \times 10^6$, respectively, from left to right. These fractograms were obtained using the normal mode of operation of a thermal FFF system for which the flow rate was $\dot{V} = 0.075$ mL/min, and the temperature drop was $\Delta T = 10°$ C.

Polymers of high molecular weight including many above 1,000,000, can be fractionated in the normal mode of thermal FFF by reducing $\Delta T$ and maintaining low flowrates. FIG. 4 shows the signals obtained in this manner for $2.8 \times 10^6$ and $4.1 \times 10^6$ molecular weight polystyrene at $\Delta T = 10°$ C. and a flow-rate of $\dot{V} = 0.075$ mL/min. The elution order is "normal" with the maximum of the $2.8 \times 10^6$ peak preceding the maximum of the $4.1 \times 10^6$ peak. The speed of separation here should be compared to those shown for the process of the invention as illustrated in FIG. 5.

Figure 5:
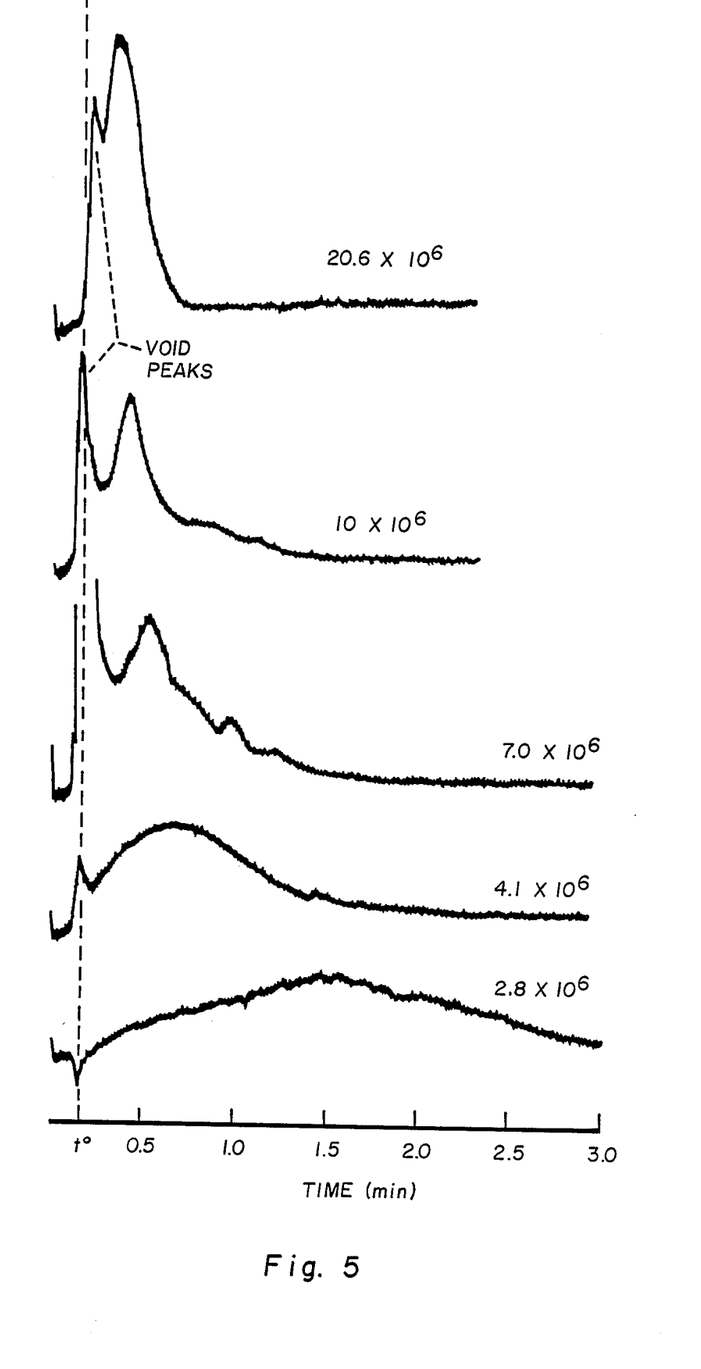
FIG. 5 is a reproduction of fractograms of high molecular weight polymers obtained under hyperlayer conditions, wherein $\dot{V} = 2.8$ mL/min and $\Delta T = 50°$ C.

FIG. 5 discloses fractograms of the high molecular weight polymers fractionated according to the process of the invention under hyperlayer conditions, specifically $\dot{V} = 2.8$ mL/min and $\Delta T = 50°$ C. The rapid rate of separation of the high molecular weight polymers is clearly illustrated by this Figure.

DETAILED DESCRIPTION OF THE INVENTION

The present invention is best described in relationship to the invention entitled "Steric Field-Flow Fractionation"-U.S. Pat. No. 4,214,981.

In the normal mode of operation of field-flow fractionation, the species to be separated are driven to one wall (the accumulation wall) of a narrow channel by external field-generated primary driving forces. Here they rapidly form a thin equilibrium cloud (whose concentration decreases exponentially away from the wall) based on the opposing fluxes of field-driven motion and diffusion (See FIG. 3A). The precise thickness of the cloud is determined by the strength of the field and the magnitude of its interaction with the species. In general, the interaction of a species with the field depends on molecular weight or particle size. For most fields or gradients the highest molecular weight species are driven most forcefully toward the wall and consequently form the thinnest equilibrium clouds adjacent to the wall.

Upon the initiation of flow through the channel, the entrained species are carried along the channel axis. However, since the flow profile is nonuniform (generally parabolic as shown in FIG. 3), the highest molecular weight species closest to the wall is caught up in the slowest streamlines immediately next to the wall and is therefore displaced downstream more sluggishly than other species. Accordingly, separation takes place in the channel; the lower molecular weight species emerge and are detected first, followed by those of successively high molecular weight.

If additional forces are now introduced into the FFF system, the mechanism of separation is subject to change. This is especially true if the new forces differ in their essential nature from the externally imposed primary driving forces that act more or less uniformly over the channel volume.

I have found a new class of forces not previously used in FFF that I observed to become important, and unexpectedly useful, when attempting to push the separation of ultra-high molecular weight polymers to extremely high levels of speed. The introduction of these forces is based on the following consideration.

The high flowrates associated with high speed FFF operation generate substantial shear gradients in the normally thin FFF channels. It is known that sufficiently high levels of shear lead to the deformation of long polymer chains; this deformation decreases the chain entropy. It is believed that the resulting entropy gradient gives rises to an apparent driving force $F_e$ which tends to displace the polymer chains into low shear regions. In the case of thin rectangular FFF channels, the shear rate decreases continuously from the wall to the channel center, the latter therefore constituting a focusing plane toward which all polymers are driven by this force. In this way $F_e$ acts in opposition to the primary driving force $F_1$ which transports the polymer chains toward the accumulation wall.

There may be other hydrodynamic forces driving polymer molecules away from the accumulation wall.

For the present purpose we define the entropic Force $F_e$ as the sum of all non-uniform flow dependent forces that tend to drive polymer molecules away from the walls of the FFF channel.

The above two forces differ in one essential characteristic that has an important bearing on the mechanism of separation when the two are combined. Whereas the primary driving force $F_1$ is essentially uniform, the entropic driving force $F_e$ is highly nonuniform, deceasing from its maximum to zero in one-half the channel thickness, normally representing a distance of $\sim 100$ μm. Therefore when conditions (field strength, flowrate, channel thickness) are adjusted such that at the accumulation wall $|F_e| > |F_1|$ some point $x_{eq}$ will exist between the accumulation wall (at $x=0$) and the center plane ($x=w/2$) for which the net force equals zero, that is $F_1 + F_e = 0$.

Figure 3B:
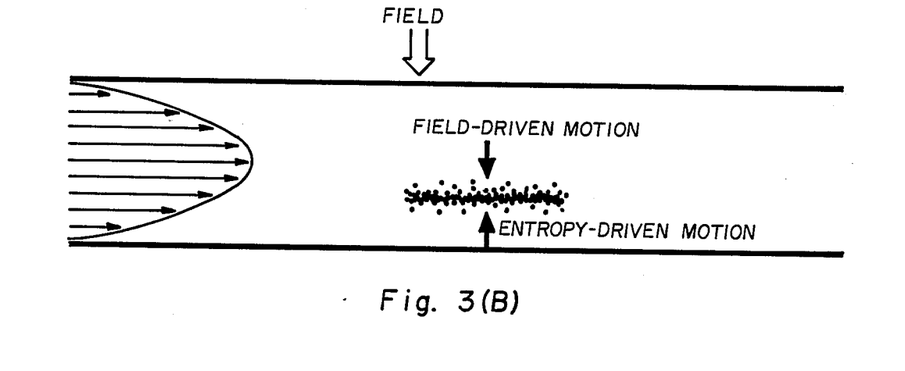

The polymer species will consequently accumulate as a band at the equilibrium position $x_{eq}$. The formation of such a band is illustrated in FIG. B. In order that this band is not unduly broadened by diffusion both of the driving forces must be sufficiently strong to sharply confine the layer of high molecular weight material. This confinement is enhanced by the sharp gradient in $F_e$.

In order to realize molecular weight selectivity by this method, the uniform and nonuniform forces utilized must depend in a different way on molecular weight. In this case the equilibrium layer will be centered at different planes for different molecular weights and the flow laminae at these planes will then displace the respective bands downstream at different velocities because of the nonuniformity of the flow profile. This requirement will be easily fulfilled for thermal and flow FFF because the driving force $F_1$ in these two cases is proportional to the friction coefficient which increases only weakly, approximately with the square root of molecular weight M. The entropy based force $F_e$ has a much stronger dependence on M. Thus, the distance of the equilibrium bands from the accumulation wall, and the associated displacement velocity of the polymer, are expected to increase with M, a trend opposite to that encountered in normal FFF.

The combination of the above forces under the conditions specified thus generates a new category of FFF separations for polymers and macromolecules. The new FFF process has significant advantages relative to the operation with either of the individual forces acting alone.

The combination of these unlike forces exhibit the following advantages. First, both of the driving forces can be flexibly adjusted relative to one another to provide the optimum distribution of the sample across the highly selective flow region, extending from the wall out to about 30% of the channel thickness. Second, these forces can be simultaneously increased to more sharply focus the component bands, thus minimizing nonequilibrium effects. Third, the high flow velocity associated with the large entropic forces and the elevated position of the component bands in the channel will combine to displace the component species rapidly through the channel, thus leading automatically to high-speed separation. Fourth, since the equilibrium layers are suspended above the wall, unfavorable polymer-wall interactions are circumvented.

The differential equilibrium layers formed in the above technique can be called hyperlayers. Hyperlayers FFF has been recognized as forming a unique category of FFF methods distinct from the normal operating mode of FFF described above. Various forces and gradients can, in theory, be used in combination to form hyperlayers. The only method that has met with substantial success is one similar to that described above, applicable to particles of micron size or greater. The nonuniform forces in the latter case consist of hydrodynamic (inertial) lift forces. Separation exhibiting both high speed and high resolution has been achieved by this approach using a crossflow driving force.

Now as to the presently claimed process, the type and size of the ultra-high molecular weight polymers and macromolecules to be separated can vary over a wide range. Generally, the polymers will have molecular weights above $1 \times 10^6$ and more preferably above $2 \times 10^6$. The polymer molecules or macromolecules may consist of random coil chains or they may have rigid backbones. The species may be soluble in either organic solvents or in aqueous liquids and they may be either synthetic or natural in origin. The method should be particularly applicable to synthetic high molecular weight polymers and to high-molecular weight biopolymers such as DNA. The molecular weights disclosed herein and in the claims are values determined by low angle laser light scattering methods.

Examples of the ultra-high molecular weight products to be separated by the process of the invention include, among others, polysaccharides, xanthan gum and various synthetic water soluble polymers of high molecular weight such as polyacrylamide and polyacrylic acids, and polymers such as polystyrenes, and the like. It should be noted that the process can be utilized for the separation of the same type polymers or of mixtures of various types of polymers or macromolecules. Alternately, preferred polymer species can be separated from lower molecular weight polymers for which entropic forces are negligible.

The carrier fluid in which the particles are to be separated can also vary over a wide range of properties. In most cases, the fluid will be that in which the particles are normally prepared or contained, such as aqueous buffers for biological macromolecules. In other cases, the carrier consists of specially prepared fluids or solutions in which the density, viscosity or other fluid characteristic is controlled in order to optimize the separation.

The concentration and amount of the polymeric material injected as the sample stream can also vary widely from extreme dilutions up to about 10% by weight or more. In most cases, the concentration will vary from about 0.01% to about 1% by weight. The amount of sample will typically vary from about 0.01 to 100 micrograms.

The external driving force preferably employed in the process of the invention include those forces or gradients which effect transverse displacement of the polymers. In operation, a component of such force or gradient is applied perpendicular to the plane of the stream flow, i.e. along the transverse axis. The forces and gradients include, among others, sedimentation forces, such as caused by centrifugation, electrical, dielectrical, cross flow force, magnetic force, temperature gradient force, and the like and combinations thereof. Preferred forces include sedimentation forces, cross flow forces, electric and temperature gradient forces, and combinations thereof.

As noted, the strength of the external driving force along with the flowrate are adjusted such that at least over part of the molecular weight range the entropic force $F_e$ at the accumulation wall and the primary driving force $F_1$ are related by the inequality $$|F_e| > |F_1|$$

The method of adjustment of the driving force depends upon the particular driving force employed. For example, for temperature gradient forces the driving force is controlled by changing the temperature drop $\Delta T$ between the two conducting metal plates forming the channel walls. For sedimentation driving forces the driving force is controlled by an adjustable spin rate.

The rate of introducing the carrier fluid is also adjusted to effect the above-noted inequality. Such adjustment is accomplished by external pump means. When a split inlet is used, both incoming flow streams are controlled independently by pump means.

As noted above, the flowrate of the fluid and the field strength of the primary externally controlled force are adjusted in relation to the channel thickness such that $|F_3| > |F_1|$ at the accumulation wall. In general, an increase in the channel thickness will require a considerable increase in the flow rate.

As noted herein before, the above noted inequality is observed generally when there is an inversion of the elution order so that the higher molecular weight polymers come out before the low molecular weight polymers.

The apparatus to be used in the process of the invention includes apparatus typically used in the FFF process as disclosed in the art, such as, for example, that shown for flow FFF in U.S. Pat. No. 4,147,621 and so much of that patent disclosure relative to the apparatus is incorporated herein by reference.

As noted, the thickness of the channel is an important factor in the FFF processes. The thickness of the channel must be very thin, and preferably less than two millimeters, to generate the necessary resolution by the FFF methods. For the present invention, the channel must be particularly thin to provide the high shear conditions needed to generate a strong entropic force $F_e$. Particularly good results are obtained when the thickness varies from about 0.05 mm to about 0.5 millimeters.

The length and breadth of the channel may vary over a wide range as long as these dimensions are considerably greater than the thickness as noted above. Increasing the length and breadth is sometimes desirable to increase throughput.

The channel should possess at least one inlet means for introducing the fluid substream containing the high molecular weight polymers to be separated. As desired or necessary the channel can also have split inlets with two inlet means for introducing substreams. As noted, pump means are employed manually or automatically to assist in the injection of the fluid streams.

To illustrate the process of the invention, the following example is given. However, it should be understood that the example is only for the purpose of illustration and does not limit the scope of the invention in any way.

EXAMPLE

This example illustrates the surprising improvement in selectivity and speed of fractionation obtained by the use of the process of the invention in the separation of very high molecular weight polymers.

The FFF channel used in this example consisted of two chrome-plated Amzirc bars with highly polished faces clamped together over a 0.003 inch (76.2 $\mu$m) mylar spacer. The channel dimensions were 2.3 cm in breadth by 34.4 cm in tip-to-tip length (the volume-based length was 31.6 cm).

The external force applied was generated by a temperature gradient obtained by using a hot bar heated by two 1100 W electric cartridge heaters controlled by computer-activated relay switches. The cold bar had holes drilled through the entire length for cold water flow. Small holes were drilled to within 0.76 mm of the surface of both bars for temperature measurement by an Omega thermistor using copper-constantan thermocouple.

Two 1-mm holes were drilled in the top copper bar running from the smooth inner face to an outer edge, one at each end, to form the inlet and outlet for the channel. The mylar spacer, cut out to form a channel, was positioned so that the two apices formed by the tapered ends aligned with the inlet and outlet holes. The connecting tubing was 0.01 in i.d. stainless steel. Samples were injected into the flowing solvent at the inlet of the channel with a Valco six-port sampling valve with either a 10 microliter or 50 microlieter sampling loop.

The polymer samples used in this example are listed in the table below. Tetrahydrofuran and ethylbenzene were used as the carrier fluid. The polystyrene polymer samples were detected by a Cole Scientific UV detector operating at 254 nm: a Servogor 120 recorder was used to monitor the detector response.

TABLE

| Polyaryewnw Sample | Mol. Wt. ($\times 10^{-6}$) |
|---|---|
| 1 | 20.6 |
| 2 | 10.0 |
| 3 | 7.0 |
| 4 | 4.1 |
| 5 | 2.8 |

In each case, the temperature gradient and the flow rate through the channel were adjusted in relation to the channel thickness such that the entropic $F_e$ and the primary drive force $F_1$ are related by the inequality $|F_3| > |F_1|$ at the accumulation wall. This inequality was confirmed by the observation that the retention time decreased with increasing molecular weight as illustrated in FIG. 5.

The experimental work established that the best results were obtained using high dilutions (about 0.3-1.0 mg/mL) of polymer in the 10 uL loop.

FIG. 5 shows the high-speed fractograms obtained for all of the above-noted polymer samples. A strikingly different result is observed relative to that shown in FIG. 4 due to the 37-fold increase in flowrate (from 0.075 mL/min to 2.8 mL/min) and the five-fold increase in $\Delta T$ from 10° C. to 50° C.

Thus, as shown in FIG. 4 the normal FFF run for the two comparable high molecular weight samples required over 40 minutes for completion, while the hyperlayer FFF run of the present invention was completed in about 3 minutes.

Not only is the speed substantially greater but surprisingly, the elution order is now inverted with the highest molecular weight polymers emerging before the lowest. This reresult is a consequence of the hyperlayer mode and establishes the superior results obtained by the present invention.

I claim as my invention:

1. A field-flow fractionation process for the fractionation of high molecular weight polymeric and macromolecular materials which comprises forcing a carrier fluid containing a small sample of the said high molecular weight material through a thin flow channel in which one of the walls of the channel becomes an accumulation wall, applying a primary externally controlled driving force transversely across the thin dimension of the channel, adjusting the flowrate of the fluid and the strength of the primary externally controlled force in relationship to the channel thickness such that at least over part of the molecular weight range the entropic force $F_e$ and the primary driving force $F_1$ are related by the inequality $|F_e| > |F_1|$ at the accumulation wall of the channel.

2. A process as in claim 1 wherein the high molecular weight polymeric components are driven to different equilibrium hyperlayer positions $x_{eq}$ by the combination of a primary driving force and an entropic lift force.

3. A process as in claim 1 wherein over part of the molecular weight range the highest molecular weight polymers elute before polymers of lower molecular weight.

4. A process as in claim 1 wherein the field-flow fractionation channel has a thin rectangular shape.

5. A process as in claim 1 wherein the field-flow fractionation channel consists of a thin open or concentric tube.

6. A process as in claim 1 wherein the shear rate at the accumulation wall exeeds 100 per second.

7. A process as in claim 1 wherein the primary driving force is generated by application of a temperature gradient across the channel thickness.

8. A process as in claim 1 wherein the primary driving force is generated by the crossflow of liquid.

9. A process as in claim 1 wherein the primary driving force is a sedimentation force.

10. A process as in claim 1 wherein the primary driving force is an electrical force.

11. A process as in claim 1 wherein the polymeric material has a molecular weight of at least $1 \times 10^6$.

12. A process as in claim 1 wherein the strength of the primary driving force is changed in the course of the run.

13. A procesa as in claim 1 wherein the sample consists of flexible polymeric molecules.

14. A process as in claim 1 wherein the polymeric material has a molecular weight between $1 \times 10^6$ to $100 \times 10^6$.

15. A process as in claim 1 wherein the sample consists of rigid polymer molecules.

16. A process as in claim 1 wherein the polymeric material consists of lipophilic polymer material.

17. A process as in claim 1 wherein the sample consists of water soluble polymers.

18. A process as in claim 1 wherein the sample consists of biopolymers.

19. A process as in claim 1 wherein the sample consists of DNA and associated materials.

* * * * *

UNITED STATES PATENT AND TRADEMARK OFFICE
CERTIFICATE OF CORRECTION

PATENT NO. : 4,830,756

DATED : May 16, 1989

INVENTOR(S) : John C. Giddings

It is certified that error appears in the above-identified patent and that said Letters Patent is hereby corrected as shown below:

Column 1, line 5, insert --Work on this invention was supported by funding from National Science Foundation contract CHE-880065.--

Signed and Sealed this

Twenty-fourth Day of July, 1990

Attest:

HARRY F. MANBECK, JR.

*Attesting Officer*  *Commissioner of Patents and Trademarks*